(12) United States Patent
Genosar et al.

(10) Patent No.: US 8,834,454 B2
(45) Date of Patent: Sep. 16, 2014

(54) DRUG DELIVERY DEVICE

(75) Inventors: Amir Genosar, Boulder, CO (US); Doron Aurbach, Bnei Brak (IL); Elena Markevich, Rishon Lezion (IL); Grigory Salitra, Rehovot (IL); Jonathan Goldstein, Jerusalem (IL); Mikhail Levi, Givat Shmuel (IL); Niles Fleischer, Rehovot (IL); Yehuda Bachar, Givat Shmuel (IL); Yossi Aldar, Tel Aviv (IL)

(73) Assignee: SteadyMed Ltd., Tel Aviv (IL)

( * ) Notice: Subject to any disclaimer, the term of this patent is extended or adjusted under 35 U.S.C. 154(b) by 841 days.

(21) Appl. No.: 12/299,602

(22) PCT Filed: May 6, 2007

(86) PCT No.: PCT/IL2007/000548
§ 371 (c)(1),
(2), (4) Date: Jul. 1, 2009

(87) PCT Pub. No.: WO2007/129317
PCT Pub. Date: Nov. 15, 2007

(65) Prior Publication Data
US 2010/0022992 A1     Jan. 28, 2010

(30) Foreign Application Priority Data

May 7, 2006 (IL) .......................................... 175460

(51) Int. Cl.
*A61K 9/22* (2006.01)
*A61M 5/20* (2006.01)
*A61M 5/145* (2006.01)
*A61M 5/142* (2006.01)
*A61M 5/172* (2006.01)

(52) U.S. Cl.
CPC ... *A61M 5/2046* (2013.01); *A61M 2005/14513* (2013.01); *A61M 2205/8206* (2013.01); *A61M 5/14586* (2013.01); *A61M 5/14276* (2013.01); *A61M 2005/14204* (2013.01); *A61M 2005/14252* (2013.01); *A61M 2205/35* (2013.01); *A61M 5/1723* (2013.01); *A61M 5/14248* (2013.01); *A61M 2230/201* (2013.01); *A61M 5/1452* (2013.01)
USPC ........ 604/890.1; 604/141; 604/143; 604/145; 604/891.1

(58) Field of Classification Search
USPC .................... 604/141, 143, 145, 890.1, 891.1
See application file for complete search history.

(56) References Cited

U.S. PATENT DOCUMENTS 4,886,514 A * 12/1989 Maget ........................ 604/891.1
5,062,834 A    11/1991 Gross et al.
(Continued)

FOREIGN PATENT DOCUMENTS

DE       36 21 846 A1    8/1998
DE       198 09 483 A1    9/1999
(Continued)

OTHER PUBLICATIONS

International Search Report of Sep. 18, 2007 for PCT application No. PCT/IL2007/000548.
(Continued)

*Primary Examiner* — Emily Schmidt
(74) *Attorney, Agent, or Firm* — Kilpatrick Townsend & Stockton LLP

(57) ABSTRACT

The present application provides a drug-delivery device comprising a drug reservoir chamber 16, containing a substance to be delivered, in fluid connection with a drug administration means 18, and an electrically-controlled battery unit 10 comprising at least one displacement-generating battery cell 19 coupled to the drug reservoir chamber 16 by a coupling means 14, the arrangement being such that the displacement derived from the battery unit 10 is conveyed by the coupling means 14 to the drug reservoir chamber 16 such that the substance is expelled from the drug reservoir chamber 16 towards the drug administration means 18.

46 Claims, 14 Drawing Sheets

(56) References Cited

U.S. PATENT DOCUMENTS

| | | |
|---|---|---|
| 5,108,852 A | 4/1992 | Tomantschger et al. |
| 5,109,850 A | 5/1992 | Blanco et al. |
| 5,318,557 A | 6/1994 | Gross |
| 5,354,264 A | 10/1994 | Bae et al. |
| 5,436,372 A | 7/1995 | Yoshida et al. |
| 5,438,249 A | 8/1995 | Chang et al. |
| 5,505,706 A | 4/1996 | Maus et al. |
| 5,527,288 A | 6/1996 | Gross et al. |
| 5,643,207 A | 7/1997 | Rise |
| 5,677,083 A | 10/1997 | Tomiyama |
| 5,814,020 A | 9/1998 | Gross |
| 5,848,991 A | 12/1998 | Gross et al. |
| 5,980,741 A * | 11/1999 | Schnell et al. ............... 210/188 |
| 6,186,982 B1 | 2/2001 | Gross et al. |
| 6,322,532 B1 | 11/2001 | D'Sa et al. |
| 6,377,848 B1 | 4/2002 | Garde et al. |
| 6,400,489 B1 | 6/2002 | Suzuki et al. |
| 6,465,125 B1 * | 10/2002 | Takami et al. ............... 429/127 |
| 6,506,520 B1 | 1/2003 | Inoue et al. |
| 6,534,218 B1 | 3/2003 | Okada et al. |
| 6,537,250 B1 | 3/2003 | Kriesal |
| 6,577,039 B2 | 6/2003 | Ishida et al. |
| 6,589,229 B1 | 7/2003 | Connelly et al. |
| 6,982,514 B1 | 1/2006 | Lu et al. |
| 7,242,134 B2 | 7/2007 | Wallace et al. |
| 7,541,715 B2 | 6/2009 | Chiang et al. |
| 2002/0169439 A1 | 11/2002 | Flaherty |
| 2003/0014014 A1 | 1/2003 | Nitzan |
| 2004/0059282 A1 | 3/2004 | Flock et al. |
| 2004/0068224 A1 | 4/2004 | Couvillon et al. |
| 2004/0115068 A1 | 6/2004 | Hansen et al. |
| 2005/0096587 A1 | 5/2005 | Santini, Jr. et al. |
| 2006/0069344 A1 | 3/2006 | Southam et al. |
| 2006/0102455 A1 * | 5/2006 | Chiang et al. ............... 200/181 |

FOREIGN PATENT DOCUMENTS

| | | |
|---|---|---|
| EP | 0 676 214 | 10/1995 |
| JP | 02-131376 | 5/1990 |
| JP | 04-127885 | 4/1992 |
| WO | WO 97/10012 | 3/1997 |
| WO | WO 01/21234 A | 3/2001 |
| WO | WO 2004/067066 A1 | 8/2004 |
| WO | WO 2005/124918 A2 | 12/2005 |

OTHER PUBLICATIONS

Written Opinion of Sep. 18, 2007 for PCT application No. PCT/IL2007/000548.

Lee et al., "Battery dimensional changes occurring during charge/discharge cycles—thin rectangular lithium ion and polymer cells," Journal of Power Sources, 2003;119-121:833-837.

Notice of Opposition to a European Patent of EP Patent No. 2 015 806 B1, dated Jun. 1, 2010, 16 pages total.

European Patent Office, "Opposition Division Decision of European Patent No. EP-B-2 015 806," dated May 5, 2012, 15 pages.

Fairbairn, A., "Statement of Grounds of Appeal pertaining to European Patent No. 2 015 806," Sep. 12, 2012, 13 pages.

\* cited by examiner

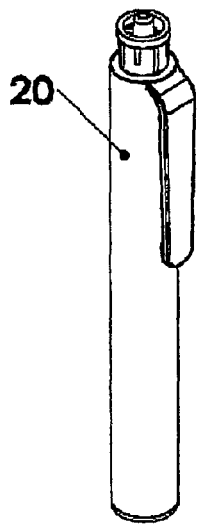
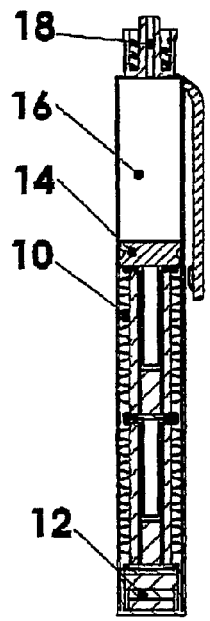
Fig. 5a        Fig. 5b
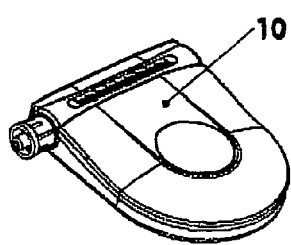 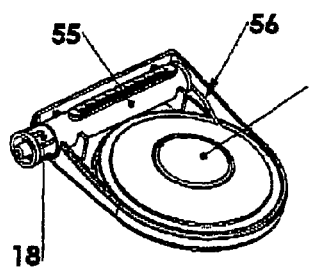 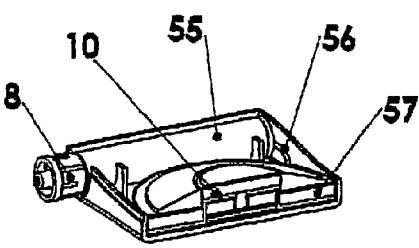
Fig. 5c        Fig. 5d        Fig. 5e

DRUG DELIVERY DEVICE

FIELD OF THE INVENTION

The present invention relates to the field of drug-delivery and relates to a drug-delivery device driven by an electrically-controlled displacement-generating battery cell. More particularly, this invention relates to a displacement-generating battery cell which drives a drug-delivery mechanism, wherein the delivery rate can be very precisely controlled by an electrical circuit.

BACKGROUND OF THE INVENTION

In the field of battery cells, the volume change generated as the battery charges or discharges is a known yet undesirable side effect, said effect being mentioned in the prior art. For example, US Patent Application 20040115530 describes a method of preventing the detrimental effects of the volume change of the active material in a lead-acid battery cell. In a co-pending patent application IL169,807 by some of the same inventors of this application, herein incorporated by reference, the concept of making use of such so-called "undesirable" volume changes in order to drive a drug-delivery device is described. However, said co-pending application exploits a relatively small volume change (of the order of 10%) as known from traditional battery chemistries, and thus requires a hydraulic or other coupling mechanism in order to exploit the relatively small volume change in an effective manner.

Accordingly, the achievement of a novel battery cell capable of a significant volume change (that is one capable of effectively driving a drug delivery device and herein referred to as a "displacement-generating battery") allows for a unique, beneficial, simpler and therefore more inexpensive solution for drug-delivery devices to be attained. Notably, such a drug-delivery device, in its simplest embodiment, would not require any mechanical or hydraulic amplification and thus would represent an advance in the art, as it would enable direct displacement of a drug in a reservoir within said drug-delivery device by said battery cell. In addition, since the displacement generated by said battery is directly related to the accumulated electric discharge in the battery, the extent of the displacement of a drug in a reservoir can be very accurately controlled.

It is therefore the object of the present invention to provide a drug-delivery device driven by such a displacement-generating battery.

It is still further object of the present invention to provide a drug-delivery device whose delivery rate and volume of drug delivered is accurately controlled by an electrochemical reaction, and specifically, by an electrochemical reaction that causes a volume change that actuates the delivery of the drug.

It is still further object of the present invention to provide a displacement-generating battery that is used as an actuator which transmits a displacement resulting from an electrochemical reaction via a coupling component in such a manner that a drug contained within a drug reservoir affected by the coupling is forced through an administration means into the body of a patient.

It is a further object of the invention that said drug-delivery be relatively insensitive to temperature and ambient pressure changes.

It is a still further object of this invention to provide a drug-delivery device with a minimum of moving parts.

It is a still further object of this invention to provide a drug-delivery device where the displacement of the drug chamber can be inherently determined from the state of discharge of the battery.

It is a still further object of this invention to provide a drug-delivery device which does not suffer from a lag in response time.

It is a still further object of this invention to provide a drug-delivery device which is inherently waterproof.

It is still further object of the present invention to provide a drug-delivery device where control and maintenance issues are simpler than in existing approaches and with less potential failure modes.

It is still further object of the present invention to provide a drug-delivery device in which the displacement-generating battery also provides the power to operate the electronics of the device thus advantageously obviating the need for having a further battery cell to power the electronics of the drug-delivery device and so the device is simplified, made more efficient, and lowered in cost.

These and other objects of this invention will become more evident in the summary of the invention and in the description of the preferred embodiment.

SUMMARY OF THE INVENTION

According to the present invention there is now provided a drug-delivery device comprising a drug reservoir chamber, containing a substance to be delivered, in fluid connection with a drug administration means, and an electrically-controlled battery unit comprising at least one displacement-generating battery cell coupled to said drug reservoir chamber by a coupling means, the arrangement being such that the displacement derived from said battery unit is conveyed by said coupling means to said drug reservoir chamber such that said substance is expelled from said drug reservoir chamber towards said drug administration means.

In preferred embodiments of the present invention each of said at least one displacement-generating battery cells comprises at least one volume-changing element.

Preferably the volume of each of said at least one displacement-generating battery cells is changed as its respective electrical capacity is changed.

In preferred embodiments of the present invention said coupling means is mechanical.

In some embodiments of the present invention said coupling means involves a displaceable wall applying direct displacement from said battery unit to said drug chamber.

In especially preferred embodiments of the present invention said coupling means is a common wall of the battery cell and the drug reservoir.

In further preferred embodiments of the present invention, said coupling means involves a displaceable wall applying indirect displacement from said battery unit to said drug chamber.

In a further preferred embodiment, said coupling means is hydraulic.

Thus according to a preferred embodiment of the present invention there is provided a delivery device for drugs or other substances (herein a "drug-delivery device") comprising a drug reservoir chamber having at least one displaceable wall and containing a substance to be delivered in fluid connection with a drug administration means, and a displacement-generating element, said element being an electric battery unit comprising at least one displacement generating battery cells coupled to said drug chamber by a coupling means, the arrangement being such that a change in the volume of at least one component of the electrochemistry of said battery unit (during discharge or charge of the displacement-generating battery) causes a wall of the battery unit to be displaced, which in return causes a wall of said drug chamber to be displaced such that said substance is expelled from said drug chamber towards said drug administration means.

In preferred embodiments of the present invention said drug administration means is selected from the group consisting of cannulas, cannula arrays, needle, micro-needle arrays, exit ports and transdermal patches.

Said drug-delivery device may be employed in a number of different configurations, including but not limited to: implantable devices, slow-infusion devices, disposable infusion devices, partially-disposable infusion devices and patch-pumps attached to the skin. Such drug delivery devices are useful for delivering drugs to patients which may be humans or other animals. Given the absence of motors and other such sensitive components, the drug-delivery device of the present invention is inherently simple to render waterproof. The displacement-generating battery used in said device may be either a primary cell or a secondary cell, or involve more than one cell. Where a primary cell is used, the volume change is caused by its discharge, and where a secondary cell is used, the volume change may be effected during either the charging or discharging thereof. In either case, such a displacement-generating battery is hereby defined as one in which at least one component of the battery cell undergoes a volume change of at least 20% or preferably at least 30%, as opposed to conventional batteries which are designed so that volume changes are minimized to substantially lower values. This volume change is then conveyed, either directly or hydraulically, to a displaceable wall of the drug chamber, causing the drug therein to be delivered via the administration means.

The displaceable wall of the drug chamber can take a number of forms, including but not limited to: a rigid yet displaceable section of the wall, a flexible or bellows type wall section, a liquid-liquid interface and a piston. A simple example of a chamber with a displaceable wall is a cylindrical cell with a rigid circular cap sealed against one end by means of an elastomeric gasket, said cap being capable of moving up or down as the charge/discharge proceeds. In all such cases, the displaceable section of the wall moves in response to the displacement of the wall of the displacement-generating battery. In the drug-delivery device of the present invention, said movement serves to expel a drug from a drug chamber in mechanical connection with said displaceable wall.

In a preferred embodiment of the present invention, the displacement-generating battery employed within the present invention applies direct displacement to a drug chamber wall, such that the drug contained within said drug chamber is forced through an administration means into the body of a patient. In a further preferred embodiment of the present invention, the displacement-generating battery applies direct force to a wall of a pouch or other envelope comprising the at least partially flexible or displaceable walls of the drug chamber, such that the drug contained within said drug chamber is forced through an administration means into the body of a patient. In a further preferred embodiment, the displacement-generating battery employed within the present invention pushes a piston of a drug chamber (either directly or via mechanical or hydraulic coupling) such that the drug contained within said drug chamber is forced through an administration means into the body of a patient. Said administration means can include a conventional cannula as known in the art, or any other means whereby the drug is introduced into the body. Such means can include arrays of short cannulas such as the SimpleChoice™ patch product (SpectRx, Inc., Norcross, Ga., USA), arrays of micro-needles, non-invasive transdermal devices, or auto needle insertion means. Alternatively, where the drug-delivery device of the present invention is an implantable one, the delivery means can be any exit port or tube leading from the device to the required location in the body of the patient.

The key to this drug-delivery device is a battery cell, at least one component of which undergoes a major volume change in excess of 20% and preferably in excess of 30% of its initial volume, either during charge or during discharge. In some cases, the overall change in volume of the entire battery is smaller than this amount (as one element shrinks or is depleted while another grows), but this is not important providing that it is still possible to mechanically exploit the volume-changing component by mechanically supporting the displacement-generating component while ensuring that the cell casing as a whole does not collapse or cause any other structural problem. In this manner, the full displacement of the displacement-generating component—in this case an electrode—may be exploited.

In general, such electrodes will benefit from a larger surface area, i.e. thinner sections and larger internal surface area, for example those achieved by using a pressed, pasted or sintered porous structure or one based on finer particles. This will allow easier access of ions for intercalation and enable higher rate discharges. In the case of a displacement-generating battery, not only is the degree of expansion important, but also the force developed should be adequate for drug-delivery. Internal stresses in the expanding electrode of at least 1 kg/sq cm and preferably 10 kg/sq cm should be attainable in the course of discharge or charge.

In especially preferred embodiments of the present invention at least one displacement-generating battery cells employs a chemical reaction system based on electrochemical insertion of metal ions.

Preferably each of said at least one displacement-generating battery cells employs a chemical reaction system chosen from the group including Li—Sn, (Li)LiC$_6$—Sn, Fe—LaNi$_5$, lithium-lead, lithium-antimony, lithium-silicon and lithium-bismuth.

Preferred electrochemical systems for said displacement-generating battery include but are not limited to Li—Sn and (Li)LiC$_6$—Sn; both of which are based on the phenomenon of the increase of thickness (up to 257%) of a tin (Sn) electrode under the chemical reaction with (or electrochemical intercalation of) Li ions. A third system, Fe—LaNi$_5$ (basically, a kind of a metal-hydride battery), could be used due to the expansion of the Fe electrode (estimated as 250%) during its oxidation to FeOOH. Further candidates for anodes include alloys of lithium such as (but not limited to) lithium-aluminum, lithium-magnesium, lithium-aluminum-magnesium, As will be obvious to one skilled in the art, various other displacement-generating battery chemistries can be chosen for the battery cell of this invention, subject only to the volume-changing requirements discussed above. Further candidates for battery systems include lithium-lead, lithium-antimony, lithium-silicon, lithium-bismuth and fuel cells; providing only that they achieve the volume-changing requirements discussed above. In the case of fuel cell batteries, the volume depletion of the fuel provides the volume-changing element.

Lithium based batteries use organic solvents or a polymer electrolyte together with a lithium ion-providing salt. Suitable non-limiting examples of such organic solvents include propylene carbonate, tetrahydrofuran, 2-methyl tetrahydrofuran, gamma-butrolactone, ethylene carbonate, dimethoxy ethane, dioxolane, diethyl carbonate, dimethyl carbonate, ethylmethyl carbonate, and various combinations of such solvents. Suitable non-limiting examples of electrolyte salts for such organic solvents include lithium perchlorate, lithium hexafluoroaresenate, lithium hexafluorophosphae, lithium tertrfluoroborate, $LiCF_3SO_3$, and $LiN(CF_3SO_2)_2$. In all these systems, as the discharge or charge proceeds, there is either a net volume change of the system or a large volume change in at least one electrode. Variations on the above systems may use lithium-carbon, lithium-graphite or lithium-aluminum alloys in place of the lithium electrode. An example of an electrolyte for the lithium-tin system is a solvent of a mixture of ethylene carbonate and ethyl methyl carbonate with dissolved lithium hexafluorophosphate as the ion-providing (ionizing) salt. Other lithium ion conducting electrolyte types are applicable, such as gel, polymer or solid state electrolytes. The basic volume change in these systems occurs as a result of lithium ion intercalation from the lithium electrode into the other electrode during the electrochemical reaction, which is driven by the potential difference between the electrodes. In the case of a lithium-tin battery, the tin electrode can expand by up to 257% in volume during discharge, while generating stresses of 15 kg/sq cm. This electrode expansion can be understood by comparing the densities of lithium (0.53) and tin (7.3). Where the electrochemical reaction within the displacement-generating battery is a reversible one, a battery cell of this type can also allow refilling of the drug-delivery device.

This approach to drug-delivery device design has a number of advantages. As there is no pump or motor in the conventional sense, there are very few parts, and essentially only a coupling component such as a displaceable wall between the cell and the drug chamber is a moving part. By using a minimum number of moving parts, failure modes and maintenance issues are minimized. Additionally, factors such as noise, friction, backlash and assembly tolerance issues are minimized. Accordingly, very precise control of the drug-delivery device is enabled by this design. In fact, providing that the non-displaceable walls of the battery remain rigid, the resolution of the achievable movement is limited only by the accuracy of the charge/discharge circuitry; something which can be provided to a very high degree using electronic circuitry known in the art. This is especially important in the case of implantable drug-delivery devices, where drug-delivery rates in the picoliter range per minute are required so as to be able to deliver drug quantities in the milliliter range over a period of months or years. Additionally, advantageously this approach provides the ability to determine the volume of drug delivered, purely by integrating the electric charge (that is, the current per unit time) used during charge or discharge of the battery. Despite this, it should be apparent to one skilled in the art that, where required, it is possible to further provide (a) a closed-loop or feedback control where which incorporates position-detection elements such that the information concerning the volume of drug delivered is not solely dependent on monitoring the charge/discharge performed; and (b) pressure sensors and other feedback and safety means can be incorporated into said control circuitry and logic.

In preferred embodiments said drug-delivery device further comprises a battery recharging means. In said embodiments, said drug-delivery device is a multiple-use device.

In some embodiments of the present invention, said drug-delivery device is a patch-type pump.

In said embodiments said patch-type pump is preferably attached to the body of a user by a means comprising an adhesion means, a strap, a clasp and combinations thereof.

In other embodiments of the present invention, said drug-delivery device further comprises auto-insertion means of the administration means.

In said other embodiments, said auto-insertion means preferably serves to insert the administration means.

In said other embodiments, said auto-insertion means preferably automatically activates the drug-delivery device.

In further preferred embodiments of the present invention said drug-delivery mechanism further comprises a plurality of drug chambers containing different drug components.

In said further preferred embodiments said drug-delivery device preferably includes means for the mixing of said different drug components from said plurality of drug chambers.

In especially preferred embodiments of the present invention said drug-delivery device further comprises at least one battery cell.

Preferably said drug chamber includes means enabling the intake of body fluids; said fluids serving to dilute a drug for subsequent administration by said drug-delivery device on reversion to its normal operating mode.

In other embodiments of the present invention said device further comprises means for sampling body fluids for analysis.

In still further embodiments said drug-delivery device further comprises communications means to remote devices, said communications means being selected from the group consisting of magnetic induction, infra-red, and RF devices.

In preferred embodiments of the present invention said administration means further comprises a safety feature to protect against accidental contact or injury.

In especially preferred embodiments of the present invention, said drug reservoir chamber is coupled to said battery unit via a displaceable wall; such that the volume change from said battery unit serves to control the rate of delivery of the drug.

In other preferred embodiments of the present invention said drug reservoir chamber is coupled to said battery via a piston arrangement; such that the volume change from said battery cell serves to control the rate of delivery of the drug.

Preferably said at least one battery cell is a lithium-tin battery cell where the volume change in the tin electrode on discharge of said cell causes the direct displacement of a displaceable wall of the drug chamber.

In preferred embodiments of the present invention the pressure in the drug chamber is monitored as part of the control and safety logic of the system.

The invention will now be described in connection with certain non-limitative preferred embodiments, with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Additional objects and advantages of the invention are set forth herein, or will be apparent to those of ordinary skill in the art from, the detailed description as follows. Also, it should be further appreciated that modifications and variations to the specifically illustrated and discussed features and materials hereof may be practiced in various embodiments and uses of this invention without departing from the spirit and scope thereof, by virtue of present reference thereto. Such variations may include, but are not limited to, substitutions of the equivalent steps, means, features, and materials for those shown or discussed, and the functional or positional reversal of various steps, parts, features, or the like.

Still further, it is to be understood that different embodiments, as well as different presently preferred embodiments, of this invention, may include various combinations or configurations of presently disclosed steps, features, elements, or their equivalents (including combinations of steps, features or configurations thereof not expressly shown in the figures or stated in the detailed description).

BRIEF DESCRIPTION OF THE DRAWINGS

The invention is herein described, by way of example only, with reference to the accompanying drawings, wherein:

FIG. 5 shows isometric and cross-sectional views of additional preferred embodiments of the drug-delivery device, including one in the form of a pen and one in which there is hydraulic coupling between the battery cell and the drug chamber;

DETAILED DESCRIPTION OF THE DRAWINGS

Figure 1A:
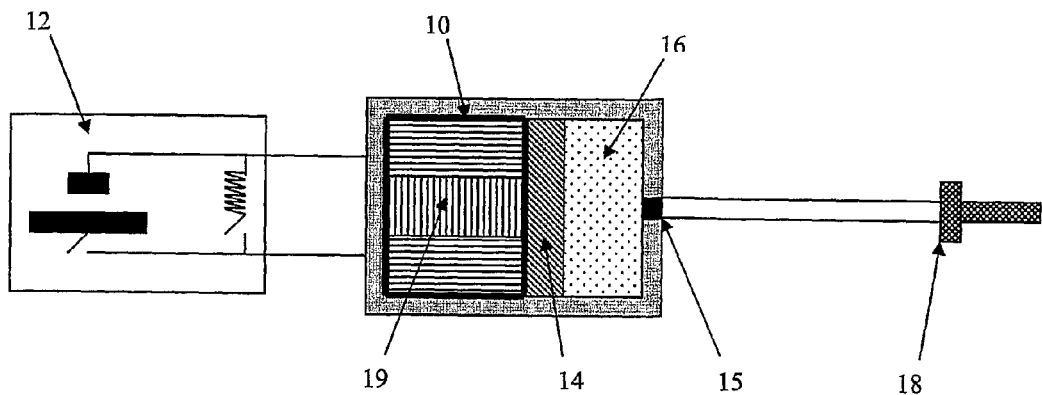
FIG. 1 provides a block diagram of the overall drug-delivery device, showing its main components.

The present invention will be described in detail according to the preferred embodiments illustrated in the accompanying drawings. Like reference numerals are used to identify identical components in the various views.

Figure 1B:
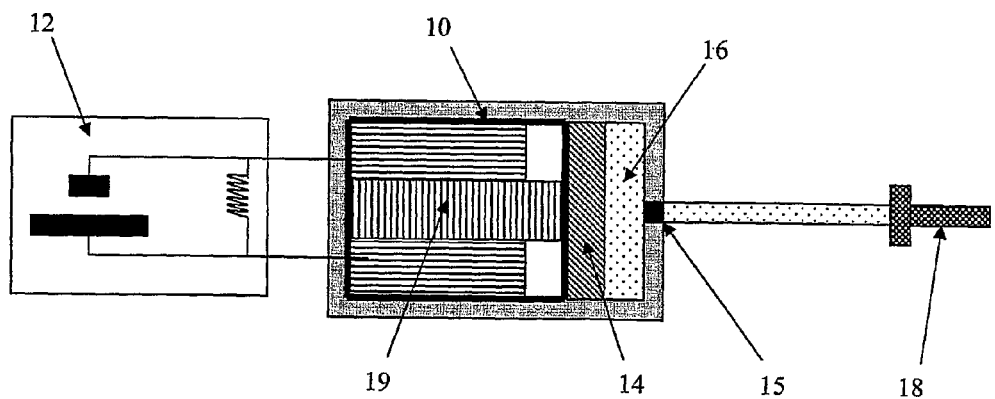

Referring to FIG. 1a, a simplified block diagram of the drug-delivery device of the present invention is shown so as to illustrate the main components involved. In this illustrative embodiment, a battery cell 10 is shown adjacent to a drug chamber 16 with a displaceable wall 14 between them, such that expansion of the volume-changing component 19 of the battery 10 causes said displaceable wall 14 to decrease the volume of the drug chamber 16. The battery 10 is activated and controlled by the control circuit 12; the activation of said battery 10 causing its volume-changing component 19 to expand in this example. Said expansion causes the drug chamber 16 to contract such that the drug is expelled through the drug administration means 18. In a preferred embodiment, said expulsion takes place via a valve 15 leading to drug administration means 18. Referring now to FIG. 1b, the situation after the battery 10 has been activated is shown, illustrating the significant change in volume of its volume-changing component 19. Note that, depending on the battery chemistry, the electric circuit will either discharge the battery 10 in order to cause the volume change, or charge the battery in order to achieve this change. For this reason both a battery and a resistor are shown within the block diagram of said circuit 12 for a schematic representation of its functionality. If the depletion method is used, advantageously this obviates the need for having a further battery cell to power the drug-delivery device of the present invention as the device is thereby self-powered to some extent, further reducing costs. Note also that the volume-changing component 19 of the battery cell 10 does not have to be an expanding component as shown but could, by a slightly different mechanical arrangement be a contracting component.

Figure 2A:
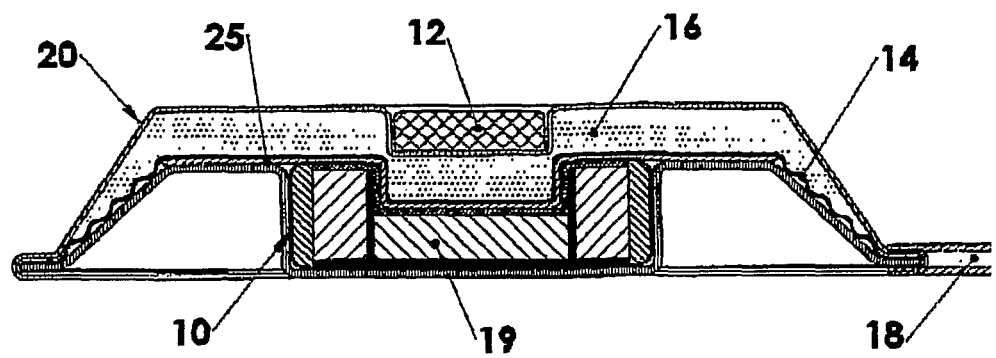
FIG. 2 provides cross-sectional and isometric views of a preferred embodiment of the drug-delivery device with a displaceable wall between the battery cell and the drug chamber.
Figure 2B:
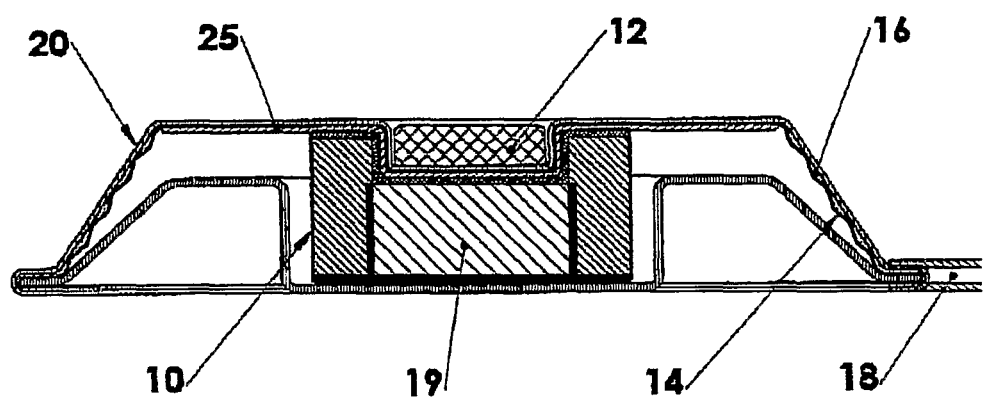

Referring now to FIG. 2, a cross-sectional view of a preferred embodiment of the drug-delivery device of the present invention is provided. FIG. 2a shows the configuration prior to activating the battery, while FIG. 2b shows the configuration of this device at the end of the device's operation. This embodiment comprises a housing 20 which contains the battery 10 and a drug chamber 16. In this embodiment, the expansion of the battery 10 moves a coupling means 25 in a shape of a plate which in turn displaces the displaceable wall 14 and reduces the volume of the drug chamber 16, causing the drug to be expelled via the administration means 18. In the preferred embodiment shown, said plate 25 is covered by a displaceable wall 14 of the drug chamber 16, said displaceable wall 14 incorporating a bellows-shaped circumference. In this preferred embodiment, the use of the displaceable wall 14 in this manner enables the optimal use of the drug chamber 16 shape in that said chamber 16 can be almost completely depleted by the displacement of said plate 25. Additionally, the bellows section of this displaceable wall 14 provides a counter-force to the force generated by the cell 10, ensuring that the displacement produced operates in a controlled fashion and is less susceptible to motion artifacts. As will be obvious to one skilled in the art, such a counter-pressure effect can alternatively be performed by the use of any other counter pressure means including but not limited to springs, or other compressible elements. The volume change under the displaceable wall 14 will be compensated either by having an opening (not shown) to the ambient air through the bottom side of the housing 20 or by using any other volume compensation means known in the art. An electronic control unit 12, which controls the discharge of the battery 10 is further incorporated in the drug-delivery device. Said control unit 12 may be interfaced with a pressure sensor (not shown) located either within the drug chamber 16, on the walls of the drug chamber 16, or along the liquid path to the administration means 18, in order to serve as the occlusion detector and send a signal back to the control unit 12 to stop the activation of the battery 10. As will be obvious to one skilled in the art, a suitable wiring arrangement (not shown) whereby both polarities of the cell 10 are connected to contacts attached to said control unit 12 is provided. Suitable materials for the housing 20 include plastics including but not limited to polyethylene (PE) and polypropylene (PP), or metal such as stainless steel; and suitable materials for the displaceable wall 14 include stainless steel, aluminum, rigid plastics or multilayer films.

Advantageously, this embodiment uses a small, lightweight battery 10 which has a small diameter relative to the diameter of the housing 20; such that the resulting device is light relative to the volume of drug it can deliver. For example the diameter of the battery 10 can be 10-30 mm, while the diameter of the drug chamber 16 is 20-60 mm correspondingly. Thus an amplification effect is achieved whereby a relatively narrow piston presses upon a drug chamber of broader proportions. Note that this does require relatively high force to be generated by the battery cell 10, but the cells described in the preferred embodiment below successfully generate this force.

Figure 2C:
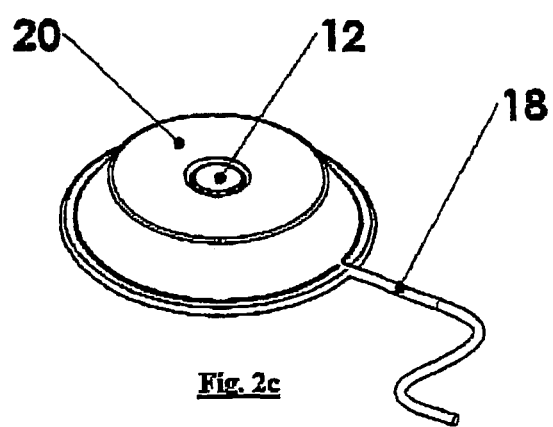

Referring now to FIG. 2c, an isometric view of the drug-delivery device of the present invention is provided, showing the housing 20, an electronic control unit 12 inserted into a recess in said housing and a delivery means 18 shown here as a thin tube. The housing 20 further comprises an air-evacuation channel (not shown) for the evacuation of air from said recess as said control unit 12 is inserted. Said control unit 12 may be a disposable, semi-disposable or permanent one. Where it is either semi-disposable or permanent, it may interlock with a location on the drug-delivery device (for example as shown in the present embodiment) so as to enable easy insertion and removal. Advantageously, making this control unit 12 re-usable reduces the cost of using the drug-delivery devices of the present invention, as then the cost of one control unit 12 may be spread over the use of many disposable devices. In a preferred embodiment, said battery cell 10 is simply discharged (in a controlled manner) by said control unit 12, making the device of the present invention essentially self-powered. Some examples of different delivery means suitable for use with this device are provided within the context of FIG. 4 below. The design can be either a circular one as shown, or a square design can be used. The unexploited space in this embodiment can, advantageously, be used for the electrical components such as sensors, buttons and/or a buzzer (all not shown). As will be obvious to one skilled in the art, in a preferred embodiment, all the elements of the drug-delivery device and its internal wiring are protected against environmental influences such as humidity.

It will be obvious to one skilled in the art that the drug does not have to be in direct contract with the displaceable wall 14 and the inner surface of the housing 20, but rather can be maintained within a flexible pouch. Suitable materials for fabricating such a drug pouch include but are not limited to high-density polyethylene (HDPE) and polypropylene (PP) or any type of multi-layer film including such materials. From a regulatory perspective, this embodiment is advantageous as it enables the drug-filling to be performed in a separately controlled and regulated fabrication environment, while the integration of the pouch into the complete drug-delivery device can potentially be performed in a less controlled environment.

Referring now to FIG. 3, a preferred embodiment of the battery cell 10 which drives the drug-delivery device is shown. In a preferred embodiment, the lithium-tin battery chemistry is employed. FIG. 3a provides a cross-sectional view of said cell showing its internal structure, while FIG. 3b provides a isometric view showing the concertina-like structure formed; both showing the initial state of the cell 10 before activation. As shown in FIG. 3a, said cell 10 comprises a flexible metal sheet housing 35 formed according to a concertina-shaped design; said housing 35 containing a lithium anode 30 and a tin cathode 19 which, in this embodiment, is the expanding element. The cell 10 further comprises a rigid cylindrical metallic mesh 33 which surrounds the tin cathode 19; there being also a separator (not shown) between the lithium anode 30 and said mesh 33. Thus the arrangement of the battery components is a concentric cylinder one, where all the remaining volume within the cell 10 is taken up by the electrolyte 32. In this preferred embodiment, the electrolyte 32 used for the lithium-tin system is a solvent of a mixture of ethylene carbonate and ethyl methyl carbonate with dissolved lithium hexafluorophosphate as the ion-providing (ionizing) salt. As the cell 10 is depleted, the lithium ions penetrate the tin cathode 19 causing it to expand. In the present embodiment, said expansion is constrained to take place primarily in the vertical direction due to the rigidity of the mesh 33 which prevents expansion to the sides. Said expansion therefore takes place against the rigid battery cap 37. In this embodiment the cap 37 serves as one pole of the battery and the housing 35 serves as the second pole. The sealing between the cap 37 and the housing 35 is electrically insulated. The wiring from the control unit will be connected to these battery poles. The housing 35 can be made from materials other than metal such as multilayer films as described in U.S. Pat. Nos. 5,134, 046, and 6,296,967) which are non-conductive, and the wiring arrangement can be as known in the art, for example as per U.S. Pat. No. 6,296,967.

Figure 3A:
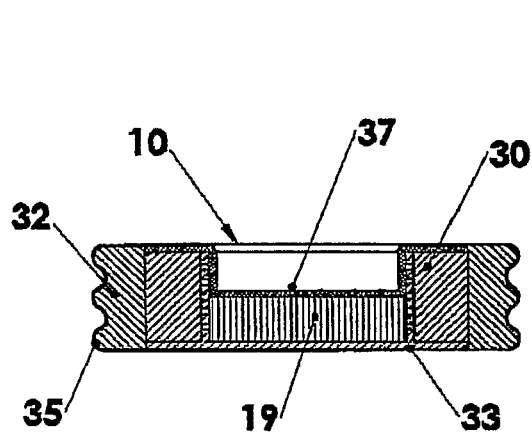
FIG. 3 provides cross-sectional and isometric views of a preferred embodiment of a battery cell for use within the present invention.
Figure 3B:
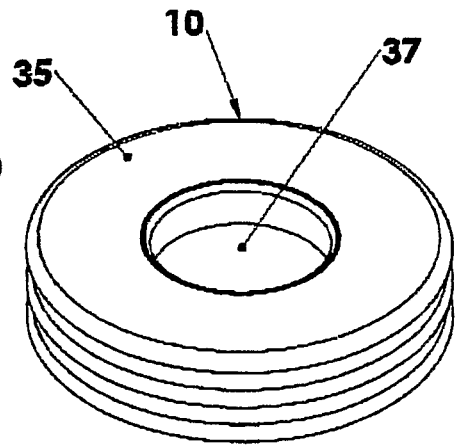
Figure 3C:
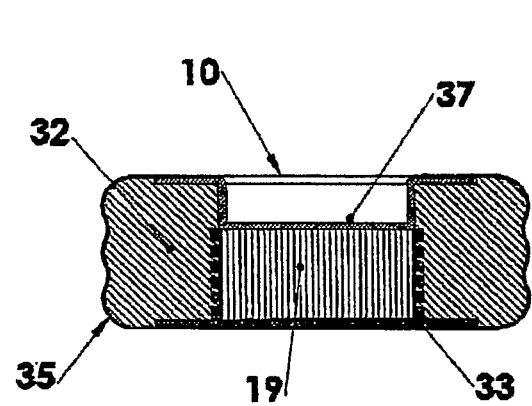
Figure 3D:
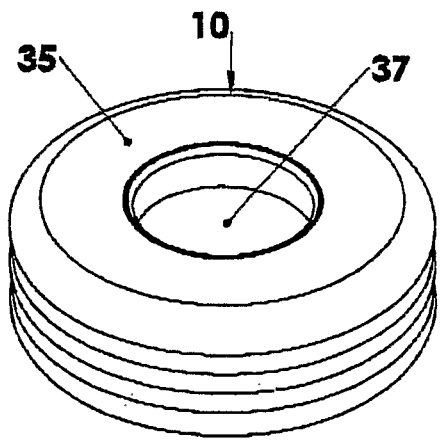

Referring now to FIGS. 3c and 3d, the state of the battery cell 10 as it is fully depleted is shown, in cross-sectional and isometric views respectively. Full depletion means that all the lithium ions have migrated into the tin cathode 19, leaving only electrolyte 32 behind. The resulting expansion of the cathode 19 has raised the position of the battery cap 37, causing an overall change in the shape of the cell. Said change is enabled by the flexible nature of the cell's housing 35. In the preferred embodiment shown, the flexible concertina shape shown is readily adaptable to the new configuration of the battery cell 10, as it adjusts to being lengthened by reducing the extent of the folds in the side walls and at the same time moving inwards in order to adapting to the overall volume change in the cell In this manner, the cell 10 becomes taller but narrower to reflect the expansion of its volume-changing component.

Note that in this preferred embodiment, the tin cathode 19 needs to be highly porous while also preserving mechanical strength. In a preferred embodiment it is prepared by making a 2:1 mixture (by volume) of Sn powder and a powder of table salt, NaCl. This mixture was pressurized in a stainless steel mold under 5 tons of pressure to form the appropriately sized pellet. This pellet was then boiled several times in distilled water, with fresh portions of distilled water being used each time, and then, finally, sonicated in distilled water for 5 minutes. After drying and weighing the pellet, full dissolution of the NaCl was verified. In this way, highly dispersed and highly porous, yet mechanically stable Sn electrodes were prepared. The constraining of the Sn pellet as it expands was solved by designing a stainless steel mesh cylinder as a holder for this pellet. The porosity enables the lithium ions to penetrate the tin (via the electrolyte), while the mesh controls the direction of said expansion. Note also that in this embodiment, as the Li is consumed, it is important to concentrate the remaining Li close to this mesh, and thus a copper (Cu) net cylinder (not shown) surrounds the lithium for this purpose.

As will be obvious to one skilled in the art, a number of different embodiments of the battery cell 10 could be applied in the design of the cell. For example, the cathode 19 need not be constrained to only expand upwards, but could alternatively be constrained to expand downwards, or be allowed to expand in both directions simultaneously. Note that in the preferred embodiment shown, the lithium anode 30 extends higher than the tin cathode 19 so as to maximize the adjacent surface between the two, in order to enhance the ion transport. However, in order to produce a lower profile cell, an embodiment in which the initial height of both electrodes is close to identical may be used. In this embodiment, the ion transport is less efficient as the tin cathode 19 expands and the protruding part of it is no longer adjacent to the lithium anode 30, but this lack of chemical efficiency is a trade-off that may be worth making in order to enable the drug-delivery device to be miniaturized more effectively. In a further preferred embodiment, the arrangement of cathode and anode may be one employing parallel layers, one above the other; in or similar to the manner of a button cell. In a further preferred embodiment, a multiplicity of anodes and cathodes may be used to produce the desired displacement.

In a further embodiment the construction of the battery cell is on a Printed Circuit Board (PCB): the electrodes will be selectively "printed" on the circuit board in contact with conductive channels. The area of the electrodes will be confined under a flexible first cover sealed to the PCB and filled with electrolyte, said first cover being the displaceable wall of the battery. In a preferred embodiment a cover is placed around said first cover and sealed against the PCB, forming the drug chamber. It is obvious to those skilled in the art that any fashion of coupling means can be introduced between the displaceable wall of the battery and the displaceable wall of the drug chamber. The control circuit can be placed on the same PCB helping to further miniaturize the assembly and increase reliability. This embodiment is advantageous for small drug chamber applications where compactization is crucial such as implantable controlled drug release devices.

Referring now to FIG. 4, a number of alternative types of administration means 18 are shown. The administration means 18 can take numerous forms depending on the type of application for which the drug-delivery device of the present invention is being used. As will be clear to one skilled in the art, the administration means 18 can be any means whereby the drug or other substance delivered by the device enters the patient's body, including but not limited to an exit port in an implantable version of the device, and a cannula, cannula array or transdermal patch for an external device. In its simplest form said administration means is simply a conduit extending from the device. Referring now to FIG. 4a, said conduit 50 leads to a Luer lock, which is a standard connector to an infusion set. Alternatively, and as shown in FIG. 4b, the Luer lock is incorporated into the housing 20 of the device. In the further preferred embodiment shown in FIG. 4c, an isometric view of an embodiment in which the administration means 18 is a cannula is shown. Said cannula is in fluid connection with the drug chamber 16, and extends either directly from the housing 20, or from a tab projecting therefrom (not shown). Said cannula may be a rigid one or an array of small rigid ones. In a further preferred embodiment, a flexible cannula such as the Teflon® type cannulas known in the art may be used. In the latter case, said cannula can be inserted into the patient's body by means of an insertion device. In a still further preferred embodiment, the cannula can be inserted into the body by a mechanism internal to the drug-delivery device of the present invention.

Figure 4A:
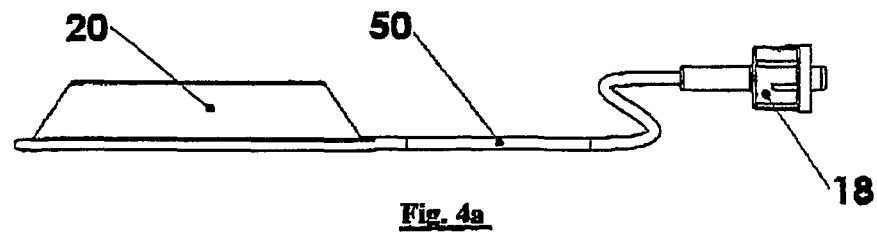
FIG. 4 provides cross-sectional and isometric views showing the integration of a number of different administration means into the drug-delivery device.
Figure 4B:
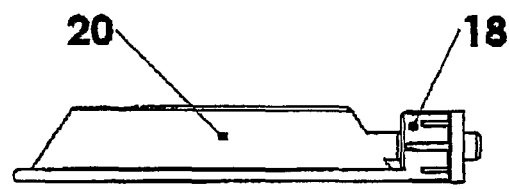
Figure 4C:
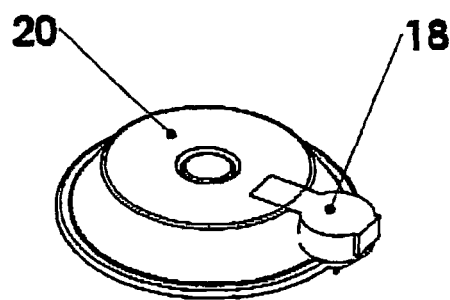
Figure 4D:
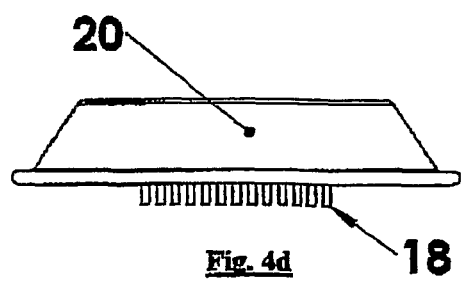

Referring now to FIG. 4d, a side view of a further preferred embodiment is provided. In this embodiment, the administration means 18 is an array of mini or micro-needles extending from the base of the housing 20 of the device. This embodiment is especially suitable for a low-profile version of the device, where only a small drug volume is required. Examples of micro-needle arrays include the Microstructured Transdermal Systems (MTS) array from 3M Drug-delivery Systems (St. Paul, Minn., USA). Advantageously, this type of array enables the disruption of the outermost layer of the skin, the stratum corneum, without causing pain; and thus the drug device of the present invention which integrates such an array can be applied to the skin in a completely painless manner.

In general the drug-delivery device of the present invention is suitable for use as a patch-pump for delivering drug volumes between 0.5 mL and 10 mL. Embodiments at the lower end of this range will be more coin-like in shape, whereas those at the higher end will be more reminiscent of the embodiments shown in FIGS. 2 and 4. A patch-pump of this nature can be applied to the skin in a number of manners, including but not limited to the use of adhesives, straps and such-like. It may also be desirable to automatically activate the drug-delivery device when the administration means 18 is applied to the skin, or when an auto-insertion means of a cannula is activated.

Referring now to FIGS. 5a and 5b, isometric and cross-sectional views (respectively) are shown of a pen-shaped preferred embodiment of the drug-delivery device of the present invention. In this preferred embodiment, a multiplicity of battery cells 10 as described above are arranged in series such that their combined displacement presses upon a displaceable wall 14. Said displaceable wall 14 acts as a piston within the drug chamber 16; the movement of said piston 14 serving to expel the drug. In a preferred embodiment of this configuration, the pen-shape is terminated at its upper end with a Luer lock serving as the administration means 18, and the electronic control unit 12 is integrated into the pen's base. This embodiment has the advantage of efficiently exploiting the available volume, such that there is little of no "dead space" within the device's housing. Additionally, the pen form-factor is well known, easy to clip on to shirt or jacket and unobtrusive; while also obviating the need to adhere the device to the skin. As will be obvious to one skilled in the art, the relative location of the components within the pen shape can easily be altered, and thus if it is preferred to have the Luer lock on the bottom and the electronics at the top, this is trivial to achieve.

A further advantage of this embodiment is that the shape of the drug chamber 16 enables a vial with an integral piston to be used. This use of such a vial is further described in connection with FIGS. 5c, 5d and 5e, in which hydraulic coupling is utilized to couple the battery cell 10 to a vial 55. This embodiment enjoys the advantage that it may use relatively standard vials, which are typically made from glass and can hold a drug for an extended period. Such a vial 55 may be inserted into the device shown by the user, thereby reducing regulatory requirements in the development of such a device. In this preferred embodiment, the expansion of the volume-changing component of the cell 10 causes the contraction of a reservoir 57 containing hydraulic fluid. On said contraction, said hydraulic fluid is expelled via hydraulic conduit 56 where it presses upon a piston (not shown) at the base of said vial 55; thereby causing the drug contained within said vial 55 to be expelled. It will be clear to one skilled in the art that the coupling between the battery cell 10 and the vial 55 may be achieved via any coupling means including but not limited to mechanical bar mechanisms, mechanical trains, pulleys, etc., resulting in either proportional motion or a more complex exponential correlation.

It will be noted that while all the above embodiments employ an expanding element within the battery cell, it will be clear to one skilled in the art that the drug-delivery device could equally well be driven by a contracting element within said cell, by changing the mechanical operation. Examples of this approach are shown in co-pending application IL169,807. Additionally, springs may advantageously be incorporated into the device in a number of configurations. For example, all the embodiments described above will achieve greater stability by having the driving force partially counterbalanced by an opposing spring. This will ensure smoother movement and provide greater artifact resistance. In a further preferred embodiment, the spring can provide the driving force while the cell serves as a brake. The advantages of this approach and further details of its implementation are described in co-pending published application WO2004067066 by one of the same authors; hereby incorporated by reference. It will also be obvious to one skilled in the art that the connection between the battery cell and the drug chamber can be any kind of mechanical, hydraulic, magnetic or other coupling means known in the art; and that said coupling action may result in either a proportional or an exponential correlation between a multiplicity of such drug chambers and a multiplicity of such cells. Note that in certain systems according to this embodiment the driving force will be the combination of the force exerted by the spring and the contraction/expansion of the cell.

Whereas the embodiments above describe relatively simple configurations of the drug-delivery device of the present invention, the general principles involved in said invention enable the implementation of a large number of further embodiments; said further embodiments addressing further issues in such devices, such as refilling, drug dilution, delivery of a multiplicity of drugs (with or without mixing) and the fabrication of sophisticated implantable versions. For example, a combination of two cells driving in opposite direction may be employed in order to enable two-way motion of a drug chamber piston in order to allow refilling of the drug chamber. Similarly, if it is desired to provide an implantable drug-delivery device which is able to work over an extended period, a second drug chamber containing a highly-concentrated form of the drug to be delivered can be incorporated. In a preferred embodiment, a small amount of said drug concentrate from the second or reservoir chamber is introduced to the drug chamber while body fluids are also introduced into said drug chamber to dilute it. In this way, further described in co-pending patent application IL169,807, the drug chamber is re-filled using a concentrate and then may resume its slow-infusion mode of operation. As will be obvious to one skilled in the art, the concentrated drug can be in either liquid or solid form, and the mechanism as described above can provide drug-delivery over an extended period without requiring external refilling. Likewise, the ability to use the drug-delivery device of the present invention to perform intake of body fluids enables said device to further incorporate various body fluid sampling and/or analysis elements.

In another preferred embodiment, the drug delivery device is driven by a displacement-generating battery, such battery increasing its volume due to an electrochemical reaction that discharges the battery; where such volume expansion actuates a coupling device to expel a drug from the drug chamber via an administration means to the patient.

In yet another preferred embodiment, the drug delivery device is driven by a displacement-generating battery containing an expanding electrode which expands due to cell discharge and whose volume expansion can be exploited to actuate a coupling device to expel a drug from the drug chamber via an administration means to the patient.

Regarding the electrical or electronic control circuit of the drug-delivery device of the present invention, it will be apparent to those skilled in the art that a wide range of electronic control systems (not shown) may be incorporated within (or interfaced to) said device. Said range includes: (a) microprocessor-controlled variable-resistance or load elements for controlled discharge of the cell; (b) removable control units that enable a semi-disposable device to be constructed whereby all or part of the control circuitry may be moved from disposable section to disposable section; (c) systems comprising a remote-control element; (d) systems that interface to a flow-control feedback element monitoring the actual drug-delivery rate, either directly or indirectly; (e) an interface control unit that receives signals related to medical parameters such as blood-glucose levels, other blood-analyte levels and body temperature; and (f) any combination of the above. Advantageously, said electronics circuit and/or electronic control systems may be at least partially powered by the very depletion of power that drives the drug-delivery device, thereby in many cases obviating the need to provide a battery to power the electronics of such a device. Additionally, in the case of an implanted device, the design may further employ embedded electronics sealed by resin casting or other sealing means known in the art, and various communication means including but not limited to magnetic coupling transmission, RF or IR transmission.

Preferred chemical systems for the battery cell of the drug-delivery device of the present invention are those which are non-gassing or in which there is minimal parasitic gas production. Nevertheless, in the case that the selected chemical reaction does generate gas and the mechanical embodiment is sensitive to gas (note that the embodiments with high counter force are less sensitive to gas) said gas may either be vented via a gas-permeable membrane or recombined via a catalytic plug such as those made by Hoppecke Battery Company, Germany. As all cell walls other than the displaceable one must remain fixed and rigid in order to maintain the accuracy of the slow-infusion device, it is important that such membrane be provided with an appropriate support structure so as not to detract from the rigid structure of the cell. These gas eliminating means are arranged in a fashion that efficiently operates in every operational orientation of the device. Suitable gas-permeable membranes include Fluoropore™ membrane from Millipore Inc. (Billerica, Mass., USA) and Emflon™ from Pall Inc. (East Hills, N.Y., USA).

Figure 6:
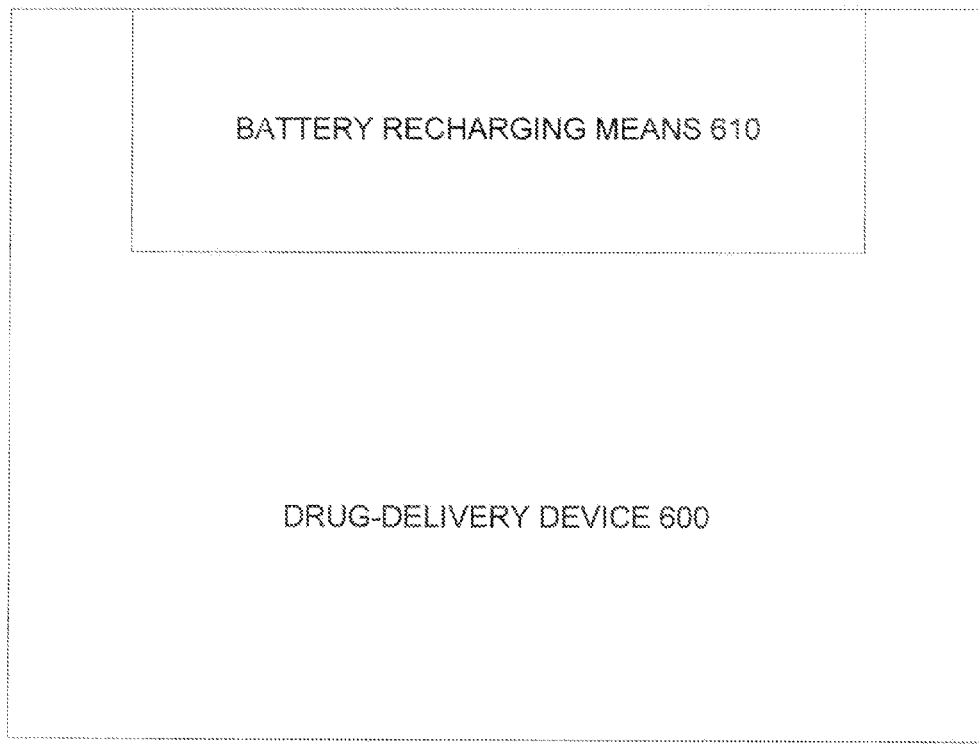
FIG. 6 shows aspects of an exemplary drug-delivery device according to embodiments of the present invention.

FIG. 6 shows aspects of an exemplary drug-delivery device according to embodiments of the present invention. Specifically, FIG. 6 depicts a drug delivery device 600 comprising a battery recharging means 610.

Figure 7:
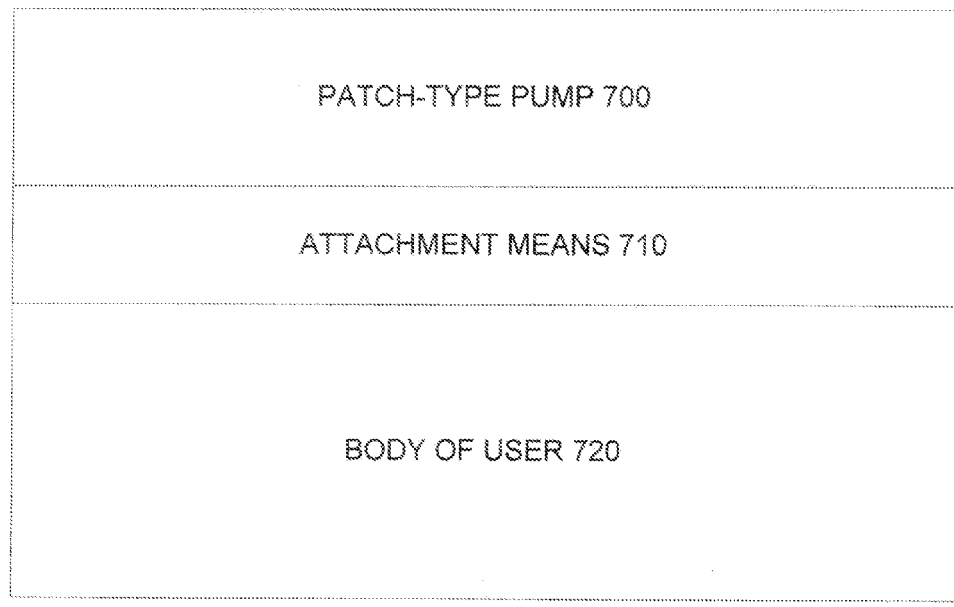
FIG. 7 shows aspects of an exemplary drug-delivery device according to embodiments of the present invention.

FIG. 7 shows aspects of an exemplary drug-delivery device according to embodiments of the present invention. Specifically, FIG. 7 depicts a drug delivery device that is a patch-type pump 700. The patch-type pump 700 is attached to the body of a user 720 by an attachment means 710. The attachment means 710 may include an adhesion means, a strap, a clasp, and combinations thereof.

Figure 8:
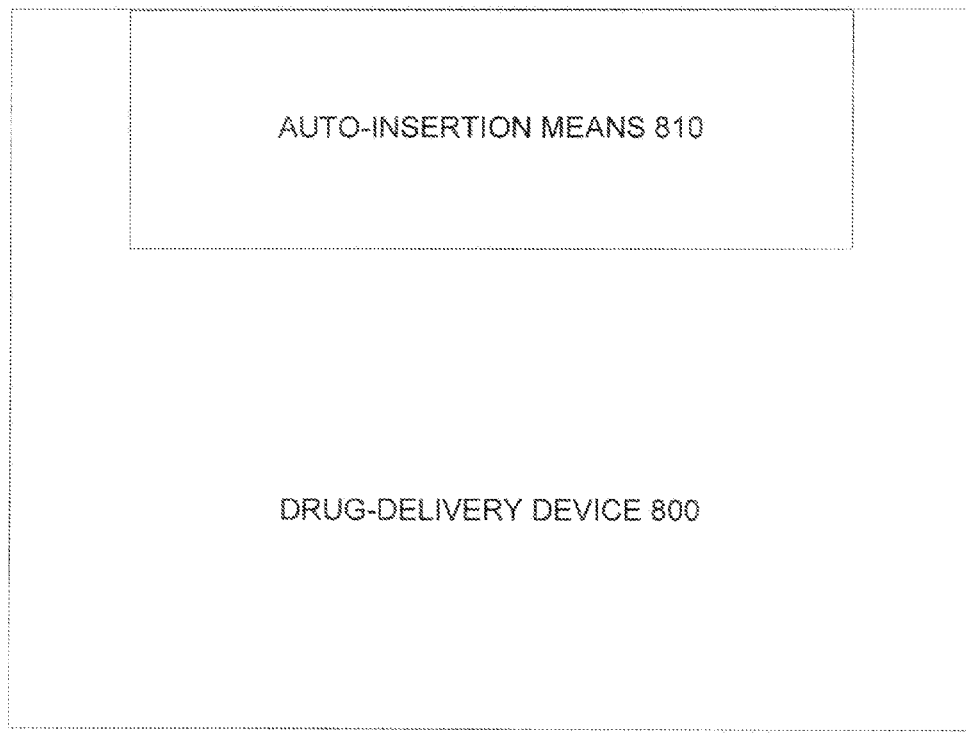
FIG. 8 shows aspects of an exemplary drug-delivery device according to embodiments of the present invention.

FIG. 8 shows aspects of an exemplary drug-delivery device according to embodiments of the present invention. Specifically, FIG. 8 depicts a drug delivery device 800 comprising an auto insertion means 810.

Figure 9:
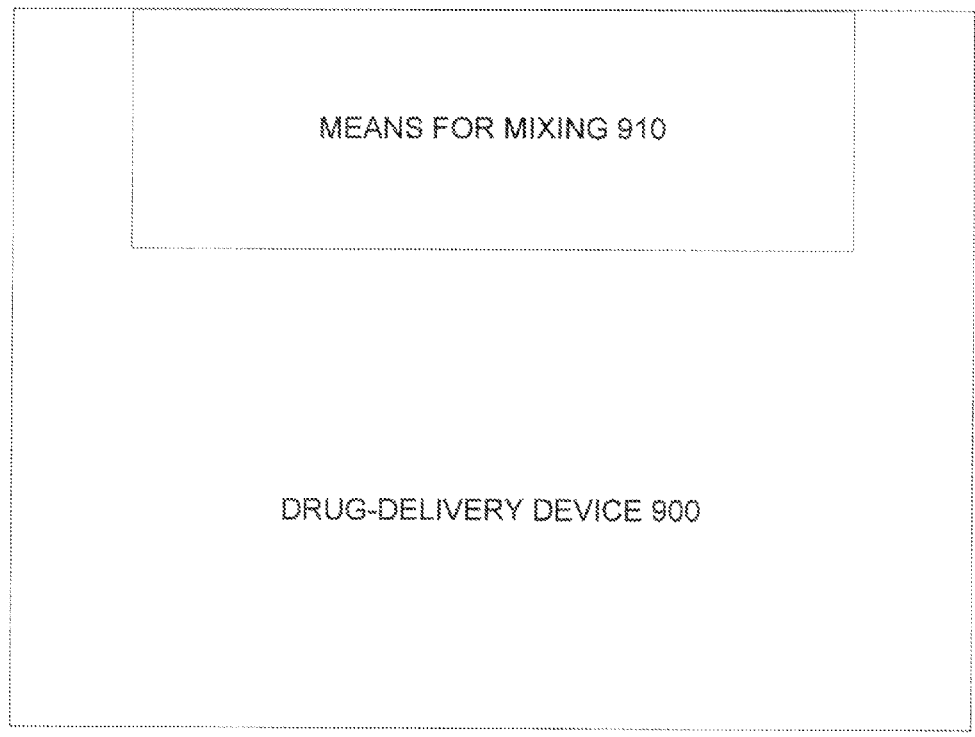
FIG. 9 shows aspects of an exemplary drug-delivery device according to embodiments of the present invention.

FIG. 9 shows aspects of an exemplary drug-delivery device according to embodiments of the present invention. Specifically, FIG. 9 depicts a drug delivery device 900 comprising a means for mixing 910.

Figure 10:
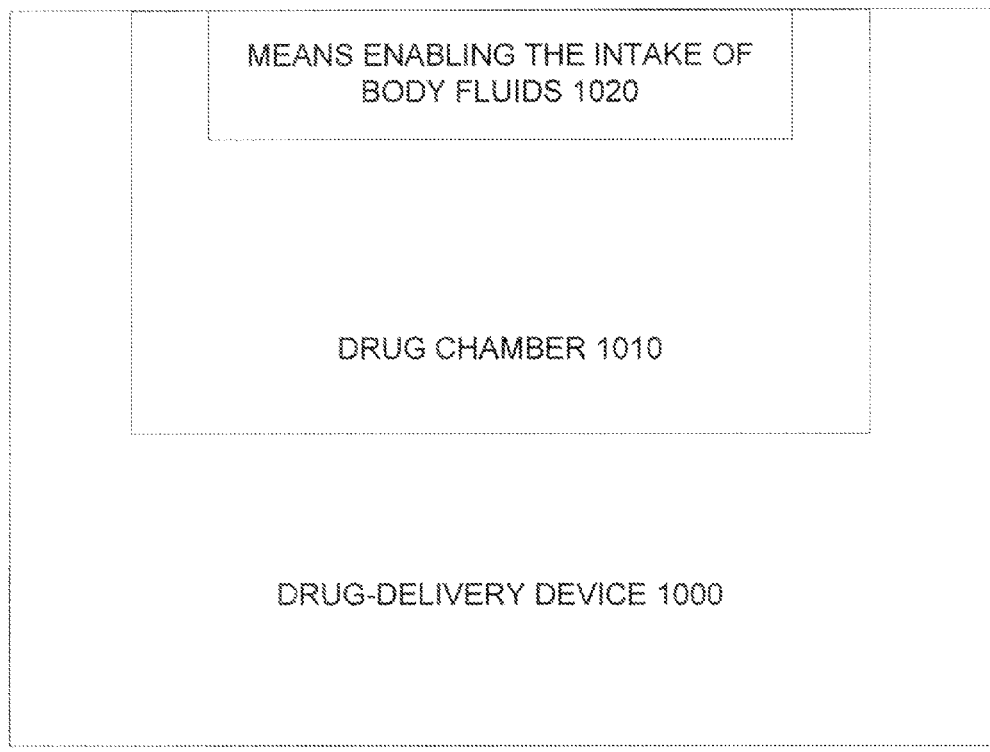
FIG. 10 shows aspects of an exemplary drug-delivery device according to embodiments of the present invention.

FIG. 10 shows aspects of an exemplary drug-delivery device according to embodiments of the present invention. Specifically, FIG. 10 depicts a drug delivery device 1000 having a drug chamber 1010, the drug chamber 1010 comprising means enabling the intake of body fluids 1020.

Figure 11:
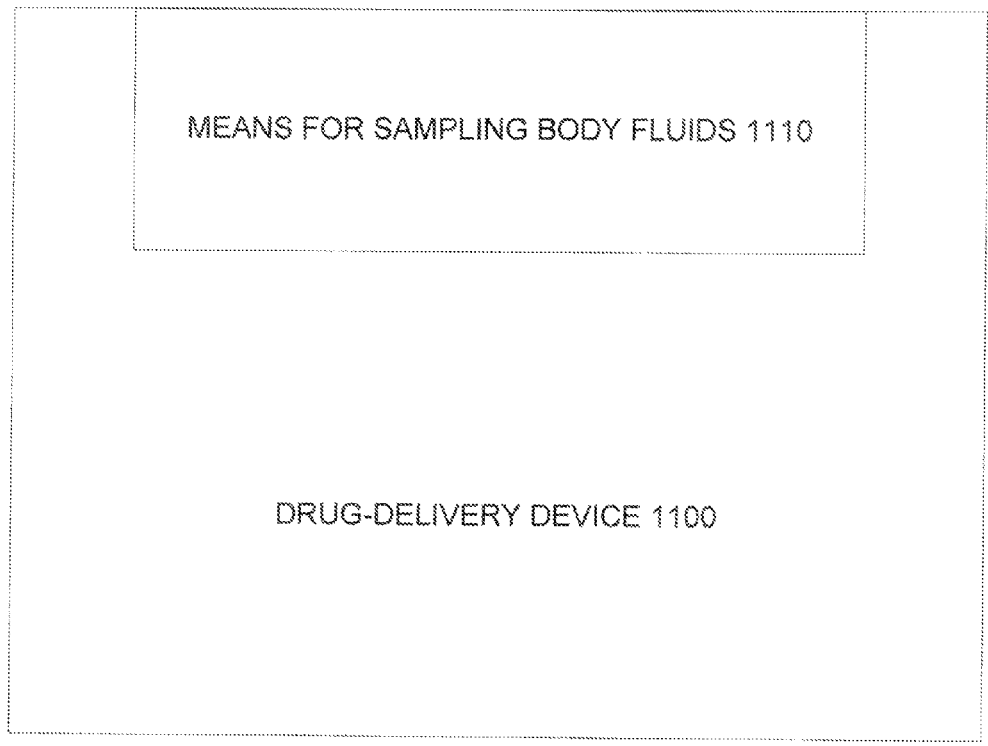
FIG. 11 shows aspects of an exemplary drug-delivery device according to embodiments of the present invention.

FIG. 11 shows aspects of an exemplary drug-delivery device according to embodiments of the present invention. Specifically, FIG. 11 depicts a drug delivery device 1100 having a means for sampling body fluids 1110.

Figure 12:
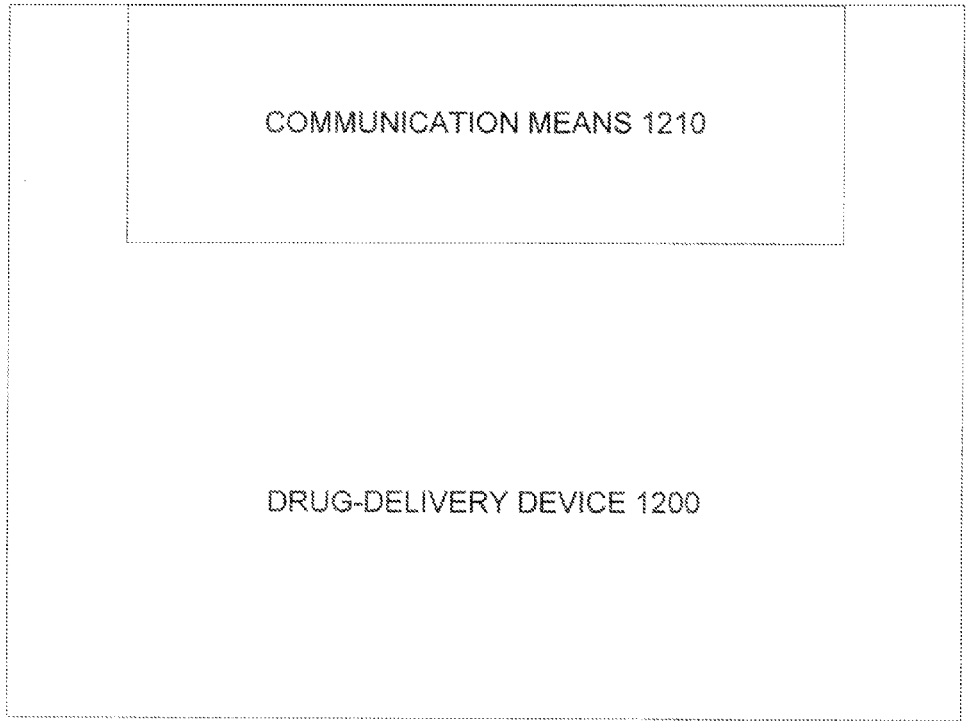
FIG. 12 shows aspects of an exemplary drug-delivery device according to embodiments of the present invention.

FIG. 12 shows aspects of an exemplary drug-delivery device according to embodiments of the present invention. Specifically, FIG. 12 depicts a drug delivery device 1200 having a communication means 1210.

Figure 13:
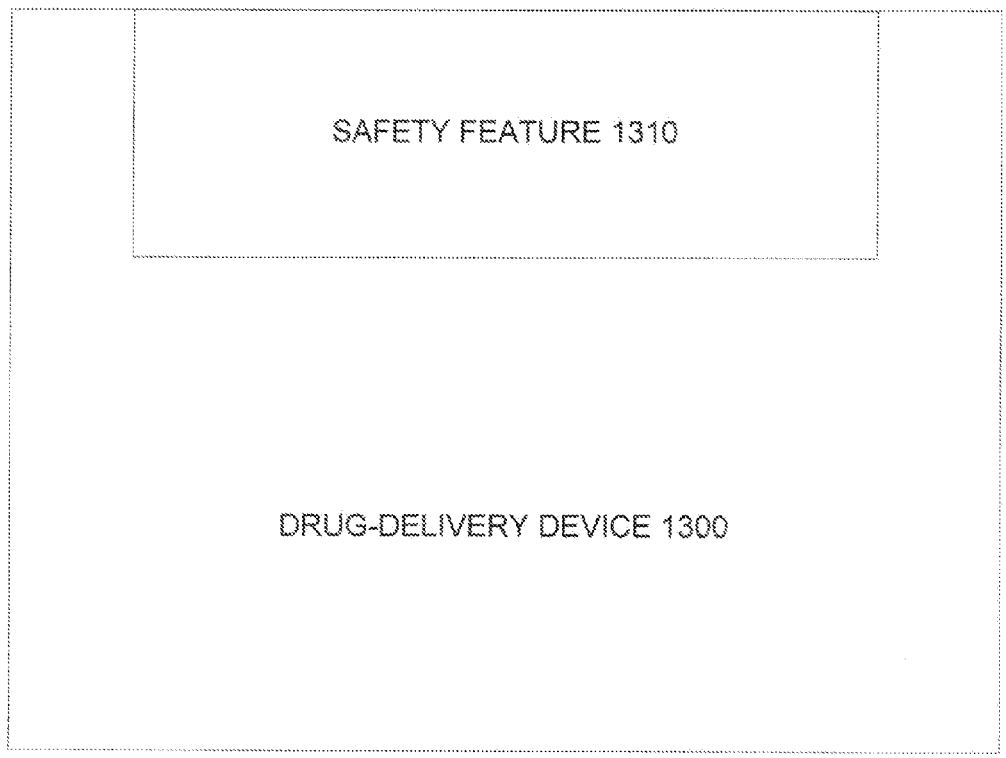
FIG. 13 shows aspects of an exemplary drug-delivery device according to embodiments of the present invention.

FIG. 13 shows aspects of an exemplary drug-delivery device according to embodiments of the present invention. Specifically, FIG. 13 depicts a drug delivery device 1300 having a safety feature 1310.

Figure 14:
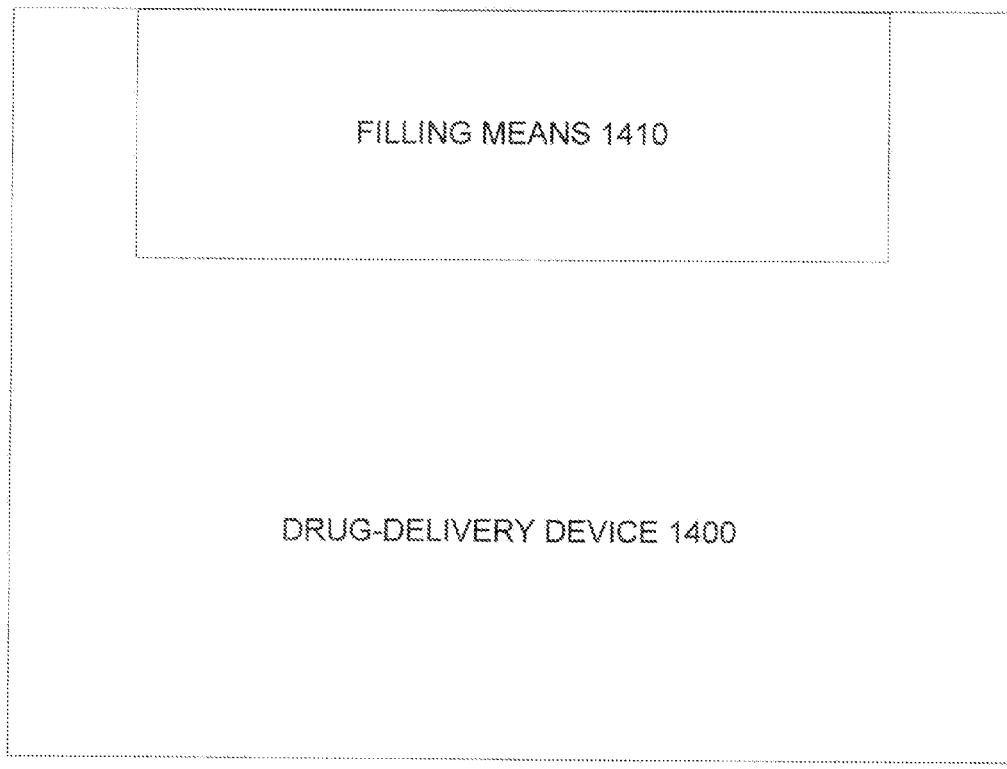
FIG. 14 shows aspects of an exemplary drug-delivery device according to embodiments of the present invention.

FIG. 14 shows aspects of an exemplary drug-delivery device according to embodiments of the present invention. Specifically, FIG. 10 depicts a drug delivery device 1400 having a filling means 1410.

A drug-delivery device may include an external filling port, and a drug chamber can be refilled via a filling port, typically by means of a septum.

Body fluids can enter a chamber through an outlet port of the chamber. The ability to use a drug-delivery device to perform intake of body fluids enables the device to further incorporate various body fluid sampling and/or analysis elements.

While the invention has been shown herein in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and devices.

What is claimed is:

1. A self-powered drug-delivery device comprising a drug reservoir chamber having a wall, containing a substance to be delivered, in fluid connection with a drug administration means, and an electrically-controlled battery unit comprising at least one displacement-generating battery cell coupled to said drug reservoir chamber by a coupling means, the at least one displacement-generating battery cell comprising an element that changes shape as a result of discharge of the battery cell so as to cause a displacement within the battery unit, the arrangement being such that the displacement derived from said battery unit is conveyed by said coupling means to cause displacement of the wall of said drug reservoir chamber reducing the volume of said drug reservoir chamber such that said substance is expelled from said drug reservoir chamber towards said drug administration means upon discharge, thereby being a self-powered drug delivery device.

2. A drug-delivery device according to claim 1 wherein said drug administration means is selected from the group consisting of cannulas, cannula arrays, needle, micro-needle arrays, exit ports and transdermal patches.

3. A drug-delivery device according to claim 1 wherein each of said at least one displacement-generating battery cells comprises at least one volume-changing element.

4. A drug-delivery device according to claim 1 wherein the volume of each of said at least one displacement-generating battery cells is changed as its respective electrical capacity is changed.

5. A drug-delivery device according to claim 1 wherein said battery unit serves to power an electrical and electronic element of said device.

6. A drug-delivery device according to claim 1 wherein said coupling means is mechanical.

7. A drug-delivery device according to claim 6 wherein said coupling means involves a displaceable wall applying direct displacement from said battery unit to said drug chamber wall.

8. A drug delivery device according to claim 7 wherein said coupling means displaceable wall is a wall of the battery cell.

9. A drug-delivery device according to claim 6 wherein said coupling means involves a displaceable wall applying indirect displacement from said battery unit to said drug chamber wall.

10. A drug-delivery device according to claim 1 wherein said coupling means is hydraulic.

11. A drug-delivery device according to claim 1 wherein said drug-delivery device is disposable.

12. A drug-delivery device according to claim 1 wherein some parts of said drug-delivery device are disposable.

13. A drug-delivery device according to claim 1 wherein said drug-delivery device is an implantable device.

14. A drug-delivery device according to claim 1 wherein said drug-delivery device further comprises a filling means.

15. A drug-delivery device according to claim 1 wherein said drug-delivery device is a multiple-use device.

16. A drug-delivery device according to claim 1 wherein said drug-delivery device is a patch-type pump.

17. A drug-delivery device according to claim 16 wherein said patch-type pump is attached to the body of a user by a means comprising an adhesion means, a strap, a clasp and combinations thereof.

18. A drug-delivery device according to claim 1 wherein said drug-delivery device further comprises auto-insertion means of the administration means.

19. A drug-delivery device according to claim 18 wherein said auto-insertion means serves to insert the administration means.

20. A drug-delivery device according to claim 18 wherein said auto-insertion means automatically activates the drug-delivery device.

21. A drug-delivery device according to claim 1 wherein said drug-delivery device further comprises a plurality of drug chambers containing different drug components.

22. A drug-delivery device according to claim 1 wherein said drug-delivery device further comprises a plurality of battery cells.

23. A drug-delivery device according to claim 13 wherein said drug chamber includes means enabling the intake of body fluids; said fluids serving to dilute a drug for subsequent administration by said drug-delivery device on reversion to its normal operating mode.

24. A drug-delivery device according to claim 1 wherein said drug-delivery device further comprises communications means to remote devices, said communications means being selected from the group consisting of magnetic induction, infra-red, and RF devices.

25. A drug-delivery device according to claim 2 wherein said administration means further comprises a safety feature to protect against accidental contact or injury.

26. A drug-delivery device according to claim 1, wherein said drug reservoir chamber is coupled to said battery unit via the drug reservoir chamber wall; such that the volume change from said battery unit serves to control the rate of delivery of the drug.

27. A drug-delivery device according to claim 1, wherein said drug reservoir chamber is coupled to said battery via a piston arrangement; such that the volume change from said battery cell serves to control the rate of delivery of the drug.

28. A drug delivery device according to claim 1 wherein the pressure in the drug chamber is monitored as part of a control and safety logic of the system.

29. A drug delivery device according to claim 1 wherein said device is selected from the group consisting of implantable devices, slow-infusion devices, disposable infusion devices, partially-disposable infusion devices and patch-pumps attached to the skin.

30. A drug delivery device according to claim 1 wherein said displacement generating battery is a primary cell.

31. A drug delivery device according to claim 1 wherein said displacement generating battery is a secondary cell.

32. A drug delivery device according to claim 1 wherein at least one component of the battery unit undergoes a volume change of at least 20%.

33. A drug delivery device according to claim 1 wherein at least one component of the battery unit undergoes a volume change of at least 30%.

34. A drug delivery device according to claim 1 wherein said drug chamber wall is provided with a rigid displaceable wall section.

35. A drug delivery device according to claim 1 wherein said drug chamber wall is provided with a flexible displaceable wall section.

36. A drug delivery device according to claim 1 wherein the displacement derived from said battery unit exerts a force of at least 1 kg/sq cm.

37. A drug delivery device according to claim 1 wherein the displacement derived from said battery unit exerts a force of at least 10 kg/sq cm.

38. A drug delivery device according to claim 1, wherein the battery cell changes in shape upon discharge of the battery cell as a result of the displacement caused by the shape-changing element, and wherein the battery cell further comprises a flexible housing that enables the change in shape of the battery cell upon discharge of the battery cell.

39. A drug delivery device according to claim 1, wherein the battery cell further comprises a flexible housing that expands in response to expansion of the shape-changing element.

40. A drug delivery device according to claim 1, wherein the shape-changing element comprises an electrode.

41. A drug delivery device according to claim 1, wherein said self-powered drug-delivery device further comprises a controller, which controller controls discharge of said battery unit, whereby on discharge, displacement derived from said battery unit is conveyed by said coupling means to cause displacement of the wall of said drug reservoir chamber, thereby reducing the volume of said drug reservoir chamber such that said substance is expelled from said drug reservoir chamber towards said drug administration means.

42. A drug delivery device according to claim 1, wherein the drug delivery device comprises no more than one displacement-generating battery cell coupled to said drug reservoir chamber by the coupling means.

43. A drug delivery device according to claim 32, wherein the volume change is reversible.

44. A drug delivery device according to claim 1, wherein the battery cell has a diameter of between 10 and 30 mm.

45. A drug delivery device according to claim 1, wherein the drug reservoir chamber has a diameter of between 20 and 60 mm.

46. A drug delivery device according to claim 1, wherein the drug reservoir chamber has a diameter between about 2 and about 6 times the diameter of the battery cell.

* * * * *